(12) United States Patent
Ahmad et al.

(10) Patent No.: US 10,376,479 B2
(45) Date of Patent: *Aug. 13, 2019

(54) ENDOXIFEN COMPOSITIONS AND METHODS

(71) Applicant: Jina Pharmaceuticals, Inc., Libertyville, IL (US)

(72) Inventors: Ateeq Ahmad, Wadsworth, IL (US); Shoukath M. Ali, Vernon Hills, IL (US); Moghis U. Ahmad, Wadsworth, IL (US); Saifuddin Sheikh, Waukegan, IL (US); Imran Ahmad, Libertyville, IL (US)

(73) Assignee: Jina Pharmaceuticals, Inc., Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/139,687

(22) Filed: Apr. 27, 2016

(65) Prior Publication Data

US 2016/0346230 A1    Dec. 1, 2016

Related U.S. Application Data

(63) Continuation of application No. 12/515,261, filed as application No. PCT/US2007/085443 on Nov. 21, 2007, now Pat. No. 9,333,190.

(Continued)

(51) Int. Cl.
*A61K 9/20* (2006.01)
*A61K 9/48* (2006.01)
(Continued)

(52) U.S. Cl.
CPC .......... *A61K 31/138* (2013.01); *A61K 9/0014* (2013.01); *A61K 9/127* (2013.01);
(Continued)

(58) Field of Classification Search
CPC ...... A61K 31/138; A61K 9/20; A61K 9/2086; A61K 9/48; A61K 9/4891; C07D 309/10
See application file for complete search history.

(56) References Cited

U.S. PATENT DOCUMENTS

| | | |
|---|---|---|
| 4,310,523 A | 1/1982 | Neumann |
| 6,090,407 A | 7/2000 | Knight et al. |

(Continued)

FOREIGN PATENT DOCUMENTS

| | | |
|---|---|---|
| WO | WO08/048194 | 4/2008 |
| WO | WO08/058156 | 5/2008 |

(Continued)

OTHER PUBLICATIONS

Assersohn et al., "Studies of the potential utility of Ki-67 as a predictive molecular marker of clinical response in primary breast cancer" Breast Cancer Res Treat 82:113-123, ( 2003).

(Continued)

*Primary Examiner* — Lakshmi S Channavajjala
(74) *Attorney, Agent, or Firm* — Casimir Jones, S.C.; Mary Ann D. Brow

(57) ABSTRACT

The present invention provides compositions containing endoxifen, formulations and liposomes of endoxifen, methods of preparation of such agents and formulations, and use of such agents and formulations for the treatment of breast cancer and other breast diseases and diseases susceptible to endoxifen. In particular, the compositions of the present invention include liposomes, complexes, vesicles, emulsions, micelles and mixed micelles of endoxifen in which the compositions further contain any of a variety of neutral or charged lipids and desirably, cholesterol and cholesterol derivatives, sterols, Z- and E-guggulsterones, phospholipids, fatty acids, vitamin D, and vitamin E. The present invention also provides methods of preparing endoxifen. The present invention provides methods for treating and preventing (Continued)

breast cancer and other breast related diseases by administrating novel formulations or compositions comprising a therapeutically effective amount of endoxifen.

1 Claim, 3 Drawing Sheets

Related U.S. Application Data

(60) Provisional application No. 60/860,788, filed on Nov. 22, 2006, provisional application No. 60/860,420, filed on Nov. 21, 2006.

(51) Int. Cl.
| A61K 31/138 | (2006.01) |
| A61K 9/19 | (2006.01) |
| A61K 9/127 | (2006.01) |
| A61K 9/00 | (2006.01) |
| A61K 31/35 | (2006.01) |
| C07D 309/10 | (2006.01) |

(52) U.S. Cl.
CPC .............. *A61K 9/19* (2013.01); *A61K 9/20* (2013.01); *A61K 9/48* (2013.01); *A61K 31/35* (2013.01); *C07D 309/10* (2013.01)

(56) References Cited

U.S. PATENT DOCUMENTS

| 6,290,991 | B1 | 9/2001 | Roser et al. |
| 6,638,767 | B2 | 10/2003 | Unger et al. |
| 9,333,190 | B2 | 5/2016 | Ahmad et al. |
| 2009/0291134 | A1* | 11/2009 | Ahmad .................... A61K 9/06 424/463 |
| 2012/0194075 | A1 | 6/2012 | Ahmad et al. |

FOREIGN PATENT DOCUMENTS

| WO | WO08/070463 | 6/2008 |
| WO | WO08/127358 | 10/2008 |

OTHER PUBLICATIONS

Fisher et al., "Tamoxifen for prevention of breast cancer: Report of the National Surgical Adjuvant and Bowel Project P-1 Study" J. Natl Cancer Insts 1998; 90:1371-88.
Furr, et al. "The pharmacology and clinical uses of Tamoxifen" Pharmacol Ther 1984; 25:127-205.
Goetz et al. "Pharmacogenetics of Tamoxifen Biotransformation Is Associated With Clinical Outcomes of Efficacy and Hot Flashes" JCO Dec. 20, 2005: 9312-9318.
Johnston et al., "Iodoxifen Antagonizes Estradiol-dependent MCF-7 Breast Cancer Xenograft Growth through Sustained Induction of Apoptosis" Cancer Research, 59, 3646-3651 (1999).
Kenny et al., Change in expression of ER, bcl-2 and MIB-1 on primary Tamoxifen and relation to response in ER positive breast cancer Breast Cancer Res Treat 65: 135-144, (2001).
Lim et al. "Endoxifen (4-hydroxy-N-desmethyl-Tamoxifen) has anti-estrogenic effects in breast cancer cells with potency similar to 4-hydroxy-Tamoxifen" Journal of Cancer Chemotherapy and Pharmacology 2005: 55: 471-478.
Lim et al., "Endoxifen, a Secondary Metabolite of Tamoxifen, and 4-OH-Tamoxifen Induce Similar Changes in Global Gene Expression Patterns in MCF-7 Breast Cancer Cells" JPET, 2006, 318:503-512.
Lino et al., "Reversible Control of Oestradiol-stimulated Growth of MCF-7 Tumours in the Athymic Mouse" Br. J. cancer, 64: 1019-1024 (1991).
Nahta et al., "Growth factor Receptors in Breast Cancer: Potential for Therapeutic Intervention" Oncologist 8: 5-17, (2003).
Osborne, "Tamoxifen in the treatment of breast cancer" N Engl J Med 1998; 339:1609-18.
Otton et al., "Venlafaxine oxidation in vitro is catalyzed by CYP2D6" Br J Clin Pharmacol 1996; 41:149-56.
Saltstein et al., "Prevention and Management of Biclutamide-induced gynecomastia and Breast Pain: Randomized Endocrinologic and Clinical Studies with Tamoxifen and Anastrozole" Prostate cancer and Prostatic Diseases 8, 75-83 (2005).
Sarkaria et al., "Tamoxifen-induced increase in the Doubling time of MCF-7 Xenografts as Determined by Bromodeoxyuridine Labeling and Flow Cytometry" Cancer Research 53, 4413-4417 (1993).
Satyavati "Guggulipid: a Promising Hypolipidaemic Agent from Gum Guggul (*Commiphora wightii*)" Economic and Medical Plant Research, 5, 47-82 (1991).
Stearns et al., "Active Tamoxifen metabolite concentrations after co-administration of Tamoxifen and the selective serotonin reuptake inhibitor paroxetine" J Natl Cancer Inst 2003; 95:1758-1764.
Stearns et al., "Hot flushes" Lancet 2002; 360:1851-61.
Suh et al., "Arzoxifene, a New Selective Estrogen receptor Modulator for Chemo prevention of Experimental Breast Cancer" Cancer Research 61, 8412-8415 (2001).
U.S. Appl. No. 60/850,446, filed Oct. 10, 2006.
U.S. Appl. No. 60/856,952, filed Nov. 6, 2006.
Lim et al. "Endoxifen has antiestrogenic effects in breast cancer cells with potency similar to 4-hydroxy-tamoxifen." Proceedings of American Cancer Research, vol. 45, 2004 abstract #3758.
Cooke, et al. "Tamoxifen Use and Osteoporotic Fracture Risk: A Population-Based Analysis," Nov. 2008 (Nov. 10, 2008); Journal of Clinical Oncology, vol. 26, No. 32, p. 5227-32.
Post, "Comparative pharmacology of bipolar disorder and schizophrenia," Sep. 29, 1999 (Sep. 29, 1999), p. 1 [online abstract]; document retrieved on Jul. 2, 2010, [retrieved from http://www.schres-Journal.com/article/S0920-9964(99)00115-2/abstract].
Steiner, et al. "Comparison of tamoxifen and clomiphene citrate for ovulation induction: a meta-analysis" Apr. 21, 2005 (Apr. 21, 2005); Human Reproduction vol. 20, No. 6 pp. 1511-1515.
Goldberg, "NCI Plans Preclinical Testing of Tamoxifen Metabolite Endoxifen for Breast Cancer" The Cancer Letter, vol. 35 No. 31 Aug. 7, 2009.
Einat et al., "Protein Kinase C Inhibition by Tamoxifen Antagonizes Manic-Like Behavior in Rats: Implications for the Develpment of Novel Therapeutics for Bioploar Disorder," Neuropsychobiology, 2007, 55:123-131.
Kisanga et al., "Tamoxifen and metabolite concentrations in serum and breast cancer tissue during three dose regimens in a randomized preoperative trial," Clin Cancer Res. 2004, 10(7):2336-43.
Majumdar et al., "In Vitro Investigations on the Toxicity and Cell Death Induced by Tamoxifen on Two Non-Breast Cancer Cell Types," J Biomed Biotechnol. 2001;1(3):99-107.
Manji et al., "Bipolar disorder: leads from the molecular and cellular mechanisms of action of mood stabilisers," British Journal of Psychiatry, 2001, 178:s107-s119, Dec. 9, 2017.
Sideras et al., Journal of Clinical Oncology, vol. 28, No. 16, Jun. 1, 2010. Copresciption of Tamoxifen and Medications That Inhibit CYP2D6.
Johnson, et al. "Pharmacological characterization of 4-hydroxy-N-desmethyl tamoxifen, a novel active metabolite of Tamoxifen," Breast Cancer Res Treat, 85(2), pp. 151-159 (2004).
Lee et al. "Quantification of tamoxifen and three metabolites in plasma by high-performance liquid chromatography with fluorescence detection: application to a clinical trial," J Chromatogr B Analyt Technol Biomed Life Sci.,791 (1-2):245-253 (2003).
Zeisiq et al., Reduction of tamoxifen resistance in human breast carcinomas by tamoxifen-containing liposomes in vivo. Anticancer Drugs. Aug. 2004;15(7):707-14.

* cited by examiner

I

ENDOXIFEN COMPOSITIONS AND METHODS

This application is a continuation of U.S. patent application Ser. No. 12/515,261, filed Jan. 8, 2010, now allowed, which is a § 371 National Entry Application of PCT/US2007/058443, filed Nov. 21, 2007, which claims priority to U.S. Provisional Application Ser. No. 60/860,420, filed Nov. 21, 2006, and 60/860,788, filed Nov. 22, 2006, each of which are incorporated herein by reference.

FIELD OF THE INVENTION

The invention relates to the use of endoxifen in the treatment of mammalian diseases. The invention also relates to liposomes and other formulations such as complexes, vesicles, emulsions, micelles and mixed micelles of endoxifen, methods of preparation, and uses, e.g., in the treatment of human and animal breast diseases. The invention in particular relates to compositions comprising endoxifen-lipid complexes, methods of preparation, and their use for the treatment of breast diseases, in particular benign and malignant breast disease, enhancing disease regression and reducing risk of patients developing breast cancer. The invention further relates to methods of preparing endoxifen and use of endoxifen prepared by inventive method in the treatment of human and animal diseases.

BACKGROUND OF THE INVENTION

Every year more than 210,000 women in the United States develop breast cancer. One in eight women in the US will develop breast cancer during their lives. Approximately 70 percent of breast cancers are fueled by estrogen, and many are treated with Tamoxifen, a drug designed to block the effects of estrogen in breast tissue.

Tamoxifen is an anti-estrogenic drug prescribed for long-term, low dose therapy of breast cancer. It has been widely used for more than 30 years for the endocrine treatment of all stages of hormone receptor-positive breast cancer (1-2). Tamoxifen has also been approved for the prevention of breast cancer (3). In women, one of the adverse events associated with Tamoxifen is hot flashes. The risk of hot flashes is two to three-folds higher among women who take Tamoxifen than it is for those who do not (4). Selective serotonin-reuptake inhibitor (SSRI) antidepressants are prescribed to treat hot flashes. However, some SSRIs, such as paroxetine and fluoxetine, are known to inhibit cytochrome P450 (CYP) 2D6 (5), an enzyme that is important for the metabolism of many drugs, including Tamoxifen. Our understanding of Tamoxifen metabolism and effect has changed clinical practice through the wide spread recognition that the co-prescription of drugs that inhibit CYP2D6 may compromise Tamoxifen efficacy. It is known that co-administration of paroxetine decreases the plasma concentration of an active metabolite of Tamoxifen, 4-hydroxy-N-desmethyl-Tamoxifen (endoxifen).

Endoxifen is generated via CYP3A4-mediated N-demethylation and CYP2D6 mediated hydroxylation of Tamoxifen (see, e.g., FIG. 3). Any drug that can be substrate of CYP3A4 or CYP2D6, especially CYP2D6 e.g., SSRIs, can decrease the level of endoxifen (6) and thus reduce the therapeutic benefits of Tamoxifen. Therefore, to avoid such drug-drug interactions, one should not give them together.

Recently, endoxifen has been shown to be anti-estrogenic in breast cancer cells and to be more potent than Tamoxifen (7). In patients treated with Tamoxifen, endoxifen is present in higher concentration (12.4 ng/mL) than 4-OH-tamoxifen (1 ng/mL) in the human plasma. The majority of genes affected by endoxifen are estrogen-regulated genes (8-9). Use of endoxifen e.g., in place of Tamoxifen, avoids several metabolic steps that rely on CYP2D6.

A strong need exists for methods to treat and to prevent breast diseases without significant adverse systemic side effects, particularly in the premenoposal population. In particular, there is a need for breast cancer treatments and preventatives that having reduced interactive effect with other medications.

SUMMARY OF THE INVENTION

The present invention provides methods and compositions for the syntheses and use of active agents such as anticancer agents. The present invention relates to methods and compositions related to the formulations and uses of endoxifen, particularly in applications related to the treatment or prevention of cancer.

In some embodiments, the present invention provides a method of treating a disease, comprising, preparing a composition comprising a therapeutically active amount of endoxifen and administering the composition. In some embodiments, the endoxifen is a free base, or is in the form of a salt. In some preferred embodiments, the endoxifen is in the form of a salt selected from the group of salts consisting of citrate, acetate, formate, oxalate, tartarate, trifluoroacetane, methane sulfonate, phosphate, sulfate, chloride, bromide, iodide, lactate, and formate. In some embodiments, the endoxifen is predominantly in a form selected from the group consisting of E-isomer, Z-isomer, and a mixture of E- and Z-isomer.

In some embodiments, method comprises preparing a complex comprising an anticancer drug and at least one lipid. In some embodiments, the anticancer drug is endoxifen. In some embodiments, the compounds of the invention are not complexed with a lipid. In some embodiments, the compound is in the form of a free base or is in the form of a salt.

In some embodiments, the present invention provides methods of preparing endoxifen, comprising reacting a compound of Formula 5 with acid, wherein the compound of formula 5 has the structure:

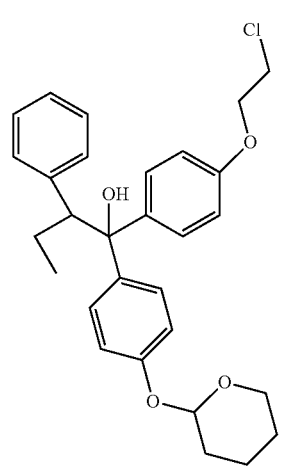

5 and, after the reaction of the compound of Formula 5 with acid, reacting the compound with methylamine. In some embodiments, the compound of Formula 5 is prepared by reacting compound of formula 4

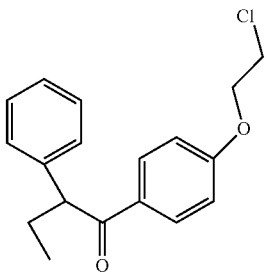

with a compound of Formula 3.

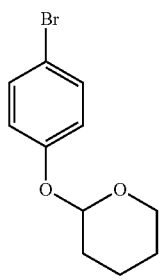

In some embodiments, the compound of Formula 3 is prepared by reacting compound of Formula 1

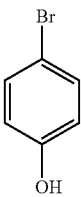

with a compound of Formula 2.

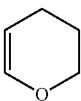

In some embodiments, the present invention provides methods of purifying the endoxifen as described above, comprising crystallizing the endoxifen and/or chromatographically treating said endoxifen to produce a purified preparation of endoxifen, wherein the purified preparation of endoxifen contains predominantly E-isomer, predominantly Z-isomer, or mixture of E- and Z-isomers of endoxifen.

As described above, in some embodiments, the invention provides endoxifen preparations comprising at least one lipid. In preferred embodiments, the at least one lipid is selected from the group consisting of egg phosphatidylcholine (EPC), egg phosphatidylglycerol (EPG), soy phosphatidylcholine (SPC), hydrogenated soy phosphatidylcholine (HSPC), dimyristoylphosphatidylcholine (DMPC), dimyristoylphosphatidylglycerol (DMPG), dipalmitoylphosohatidylcholine (DPPC), disteroylphosphatidylglycerol (DSPG), dipalmitoylphosphatidylglycerol (DMPG), cholesterol (Chol), cholesterol sulfate and its salts (CS), cholesterol hemisuccinate and its salts (Chems), cholesterol phosphate and its salts (CP), cholesterylphosphocholine and other hydroxycholesterol or amino cholesterol derivatives, cholesteryl succinate, cholesteryl oleate, polyethylene glycol derivatives of cholesterol (cholesterol-PEG), coprostanol, cholestanol, cholestane, cholic acid, cortisol, corticosterone, hydrocortisone, and calciferol, E-guggulsterone, Z-guggulsterone, mixture of E- and Z-guggulsterone, monoglycerides, diglycerides, triglycerides, carbohydrate-based lipids selected from a group consisting of galactolipid, mannolipid, galactolecithin, β-sitosterol, stigmasterol, stigmastanol, lanosterol, α-spinasterol, lathosterol, campesterol, phosphatidylcholine, phosphatidylglycerol, phosphatidylethanolamine, phosphatidylserine, phosphatdylinositol, phosphatidic acid, and pegylated derivatives of distearoylphosphatidylglycerol, dipalmitoylphosphatidylglycerol, dimyristoylphosphatidylglycerol, and dioleoylphosphatidylglycerol.

In some embodiments, a composition according to the present invention comprises endoxifen, cholesterol and/or cholesterol derivatives, and one or more phospholipids. In some preferred embodiments, the composition comprises a cholesterol derivative, and the cholesterol derivative is cholesteryl sulfate. In some embodiments, at least one of the phospholipids is hydrogenated soy phosphatidylcholine or soy phosphatidylcholine.

In some embodiments of the methods and compositions of the present invention, the composition comprises a form selected from the group consisting of powder, solution, emulsion, micelle, liposome, lipidic particle, gel, and paste form. In some preferred embodiments, the preparing of the composition comprising a complex comprises preparing said complex in a lyophilized form. In some embodiments, the preparing the complex in a lyophilized form comprises using a cryoprotectant, wherein said cryoprotectant comprises one or more sugars selected from the group consisting of trehalose, maltose, lactose, sucrose, glucose, and dextran. In some embodiments, the composition comprises a tablet or a filled capsule, wherein said tablet or filled capsule optionally comprises an enteric coating material.

In some embodiments of the treatment methods of the present invention, the disease is caused by cancer or by cancer-causing agents, while in some embodiments, the disease is benign breast disease.

In some embodiments, the administering comprises oral, intravenous, subcutaneous, percutaneous, parenteral, intraperitoneal, rectal, vaginal, and/or topical delivery said composition to said subject.

In some embodiments, the composition comprises a penetration enhancer, wherein said penetration enhancer comprises at least one saturated or unsaturated fatty acid ester.

In some embodiments, the composition comprising endoxifen is formulated in a hydroalcoholic gel, a hydroalcoholic solution, a patch, a cream, an emulsion, a lotion, an ointment, a powder or an oil.

In some embodiments, the composition comprising endoxifen is formulated in a hydroalcoholic composition containing a penetration enhancer, an aqueous vehicle, an alcoholic vehicle and a gelling agent.

In some embodiments, the hydroalcoholic composition comprises a neutralizing agent.

In some embodiments, the hydroalcoholic composition comprises endoxifen at about 0.01% to 0.20% by weight; isopropyl myristate at about 0.1% to 2.0%, preferably 0.5% to 2.0% by weight; alcohol at about 50.0% to 80.0%, preferably about 60.0% to 75.0% by weight; aqueous vehicle at about 20.0% to 60.0%, preferably 25.0% to 50.0% by weight; and gelling agent at about 1.0% to 10.0%, preferably about 0.5% to 5.0% by weight. In some embodiments, the wherein the percentage of components is weight to weight of the composition.

In some embodiments, the alcohol is ethanol or isopropanol, and constitutes in absolute form.

In some embodiments, the aqueous vehicle is a phosphate buffered solution.

In some embodiments, the gelling agent is selected from the group consisting of polyacrylic acid, hydroxypropylcellulose and a cellulose derivative other than hydroxypropylcellulose.

In some embodiments, the hydroalcoholic composition further comprises a neutralizing agent, wherein said neutralizing agent is selected from the group consisting of sodium hydroxide, potassium hydroxide, ammonium hydroxide, aminomethylpropanol, arginine, trolamine, and tromethamine, and wherein said neutralizing agent exists at a neutralizing agent/gelling agent ratio of about 1:1 to about 4:1.

In some embodiments, the invention provides methods of delivering endoxifen, comprising: providing any of the above described compositions and delivering the composition so as to expose the composition to a cell.

In some embodiments, the cell is in vivo.

In some embodiments of the invention, the host is a mammal.

The present invention also provides methods of inhibiting hormone-dependent breast carcinoma in a mammal comprising administering any of the above compositions to the mammal.

The present invention further provides methods of inhibiting a cancer in a mammal, said cancer including, but not limited to, lung cancer, colon cancer, breast cancer, leukemia, renal cancer, melanoma, cancer or the central nervous system, and prostate cancer in a mammal; the method comprising administering any of the above compositions to said mammal (e.g, a human).

The present invention further provides compositions comprising a therapeutically active amount of a complex comprising endoxifen and at least one lipid, wherein said endoxifen is a free base or is in the form of a salt.

In some embodiments, the composition comprising endoxifen is formulated in a hydroalcoholic gel, a hydroalcoholic solution, a patch, a cream, an emulsion, a lotion, an ointment, a powder or an oil.

In some embodiments, the composition comprising endoxifen is formulated in a hydroalcoholic composition containing a penetration enhancer, an aqueous vehicle, an alcoholic vehicle and a gelling agent.

In some embodiments, the hydroalcoholic composition comprises a neutralizing agent.

In some embodiments, the hydroalcoholic composition comprises endoxifen at about 0.01% to 0.20% by weight; isopropyl myristate at about 0.1% to 2.0%, preferably 0.5% to 2.0% by weight; alcohol at about 50.0% to 80.0%, preferably about 60.0% to 75.0% by weight; aqueous vehicle at about 20.0% to 60.0%, preferably 25.0% to 50.0% by weight; and gelling agent at about 1.0% to 10.0%, preferably about 0.5% to 5.0% by weight. In some embodiments, the wherein the percentage of components is weight to weight of the composition.

The present invention is not limited to the compositions and methods described above. It should be understood that variations of the above compositions and methods described elsewhere herein or that are understood by a skilled artisan in view of the present disclosure are included within the invention.

DEFINITIONS

Figure 1:
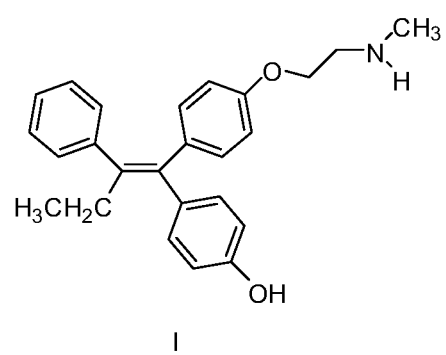
FIG. 1 diagrams compound I.

As used herein, the terms "host," "subject" and "patient" refer to any animal, including but not limited to, human and non-human animals (e.g., dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the terms "subject at risk of cancer" refers to a subject identified as being at risk for developing cancer, e.g., by prior health history, genetic data, etc.

As used herein, the term "anticancer drug" refers to an agent used to treat or prevent cancer. Such agents include, but are not limited to, small molecules, drugs, antibodies, pharmaceuticals, and the like.

As used herein, the term "effective amount" refers to the amount of an active composition (e.g., a pharmaceutical compound or composition provided as a component in a lipid formulation) sufficient to effect beneficial or desired results. An effective amount can be administered in one or more administrations, applications or dosages and is not intended to be limited to a particular formulation or administration route.

As used herein, the terms "active" or "pharmaceutically active" as used in reference to an agent, drug, composition, or compound, refers to an agent that, upon administration or application, causes a beneficial, desired, or expected result. The administration may be in one or more administrations, applications or dosages and is not intended to be limited to a particular formulation or administration route. The term is not limited to any particular level of activity.

The terms "agent" and "compound" are used herein interchangeably to refer to any atom, molecule, mixture, or more complex composition having an attributed feature. For example, an "active agent" or "active compound" refers to any atom, molecule, preparation, mixture, etc., that, upon administration or application, causes a beneficial, desired, or expected result.

As used herein, the term "treating" includes administering therapy to prevent, cure, or alleviate/prevent the symptoms associated with, a specific disorder, disease, injury or condition.

As used herein, the term "treatment" or grammatical equivalents encompasses the improvement and/or reversal of the symptoms of disease (e.g., cancer), or reduction of risk of occurrence of disease. A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., cancer, or symptoms or pathologies consistent with cancer) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompasses subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as emotional trauma, physical trauma, malnutrition, industrial hazards, or climate), to specific infective agents (such as worms, bacteria, or viruses), to inherent defect of the organism (such as various genetic anomalies, or to combinations of these and other factors.

As used herein, the term "administration" refers to the act of giving a drug, prodrug, or other active agent, or therapeutic treatment (e.g., compositions of the present invention) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), rectal, vaginal, oral mucosa (buccal), ear, by injection (e.g., intravenously, subcutaneously, intratumorally, intraperitoneally, etc.) and the like. Administration may be in one or more administrations, applications or dosages, and is not intended to be limited to a particular administration route.

As used herein, the term "co-administration" refers to the administration of at least two agent(s) (e.g., two separate lipid compositions, containing different active compounds) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutically purified" refers to a composition of sufficient purity or quality of preparation for pharmaceutical use.

As used herein, the term "purified" refers to a treatment of a starting composition to remove at least one other component (e.g., another component from a starting composition (e.g., plant or animal tissue, an environmental sample etc.), a contaminant, a synthesis precursor, or a byproduct, etc.), such that the ratio of the purified component to the removed component is greater than in the starting composition.

As used herein, the term "pharmaceutical composition" refers to the combination of an active agent (e.g., an active pharmaceutical compound) with a carrier, inert or active (e.g., a phospholipid), making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present invention may be formulated for horticultural or agricultural use. Such formulations include dips, sprays, seed dressings, stem injections, sprays, and mists.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "hydroalcoholic" as used in reference to a substance or composition indicates that said substance or composition comprises both water and alcohol.

As used herein, the term "gelling agent" refers to a composition that, when dissolved, suspended or dispersed in a fluid (e.g., an aqueous fluid such as water or a buffer solution), forms a gelatinous semi-solid (e.g., a lubricant gel). Examples of gelling agents include but are not limited to hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatin, and poloxamer.

As used herein, the term "dried" as used in reference to a composition refers to removing the solvent component or components to levels that no longer support chemical reactions. The term is also used in reference to a composition that has been dried (e.g., a dried preparation or dried composition). Those of skill in the art will appreciate that a composition may be "dried" while still having residual solvent or moisture content after, e.g., lyophilization, or that a dried composition may, after the end of a drying process, absorb moisture hygroscopically, e.g., from the atmosphere. The term "dried" encompasses a composition with increased moisture content due to hygroscopic absorption.

As used herein, the term "protective agent" refers to a composition or compound that protects the activity or integrity of an active agent (e.g., an anticancer drug) when the active agent is exposed to certain conditions (e.g., drying, freezing). In some embodiments, a protective agent protects an active agent during a freezing process (i.e., it is a "cryoprotectant"). Examples of protective agents include but are not limited to non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride.

As used herein, the term "excipient" refers to an inactive ingredient (i.e., not pharmaceutically active) added to a preparation of an active ingredient. The gelling and protective agents described herein may be referred to generally as "excipients."

As used herein, the term "kit" refers to any delivery system for delivering materials. In the context of kinase activity or inhibition assays, such delivery systems include systems that allow for the storage, transport, or delivery of reaction reagents and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an agent for use in an assay, while a second container contains standards for comparison to test compounds. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

DETAILED DESCRIPTION OF THE INVENTION

The present invention provides compositions and methods for delivering endoxifen of Formula I, e.g., to a mammalian host. In some embodiments of the present invention endoxifen is an E-isomer, while in other embodiments, it is a Z-isomer, while it is still in other embodiments, it is a mixture of E- and Z-isomers

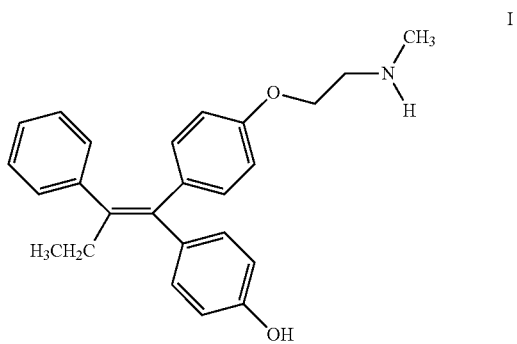

An example of the present invention includes endoxifen, analogues of endoxifen, and derivatives of endoxifen, including but not limited to endoxifen, Tamoxifen, and 4-hydroxytamoxifen. The present invention also find use with other antineoplastic agents such as paclitaxel, docetaxel, melphalan, chlormethine, extramustinephosphate, uramustine, ifosfamide, mannomustine, trifosfamide, streptozotocin, mitobronitol, mitoxantrone, methotrexate, fluorouracil, cytarabine, tegafur, idoxide, taxol, paclitaxel, daunomycin, daunorubicin, bleomycin, amphotericin, carboplatin, cisplatin, BCNU, vincristine, camptothecin, SN-38, doxorubicin, and etopside. Also included are steroidal and non-steroidal inhibitors used in cancer treatment, such as bicautamide, exemestane, formestane, letrozole, anastrazole and their analogues.

Figure 2:
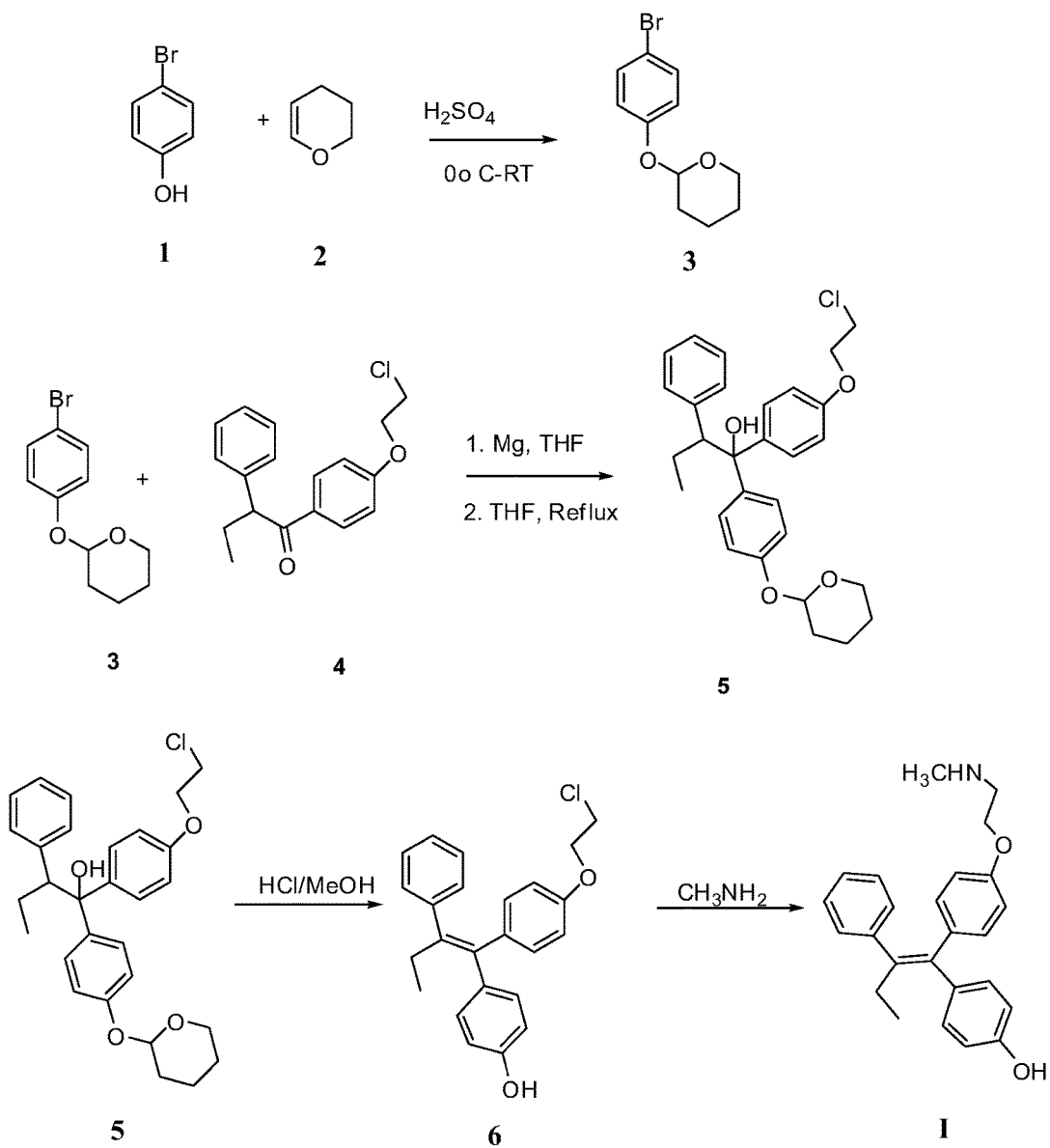
FIG. 2 diagrams embodiments for synthesis of compounds 3, 5, and I.
Figure 3:
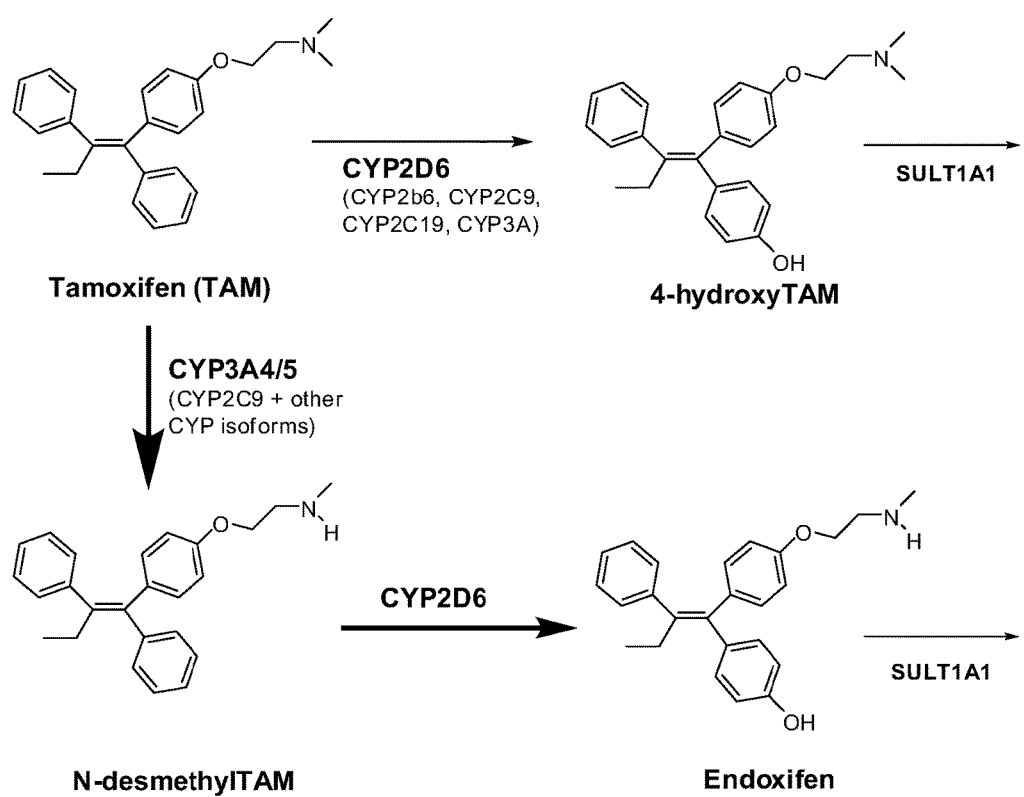
FIG. 3 diagrams portions of Tamoxifen metabolic pathways.

Endoxifen of Formula I can be prepared by any desired method for use in the treatments of the present invention but, in some embodiments, the present invention provides particular methods for the preparation of endoxifen. One preferred method of the present invention is set forth in FIG. 2. In this method, 4-bromophenol 1 is reacted with 3,4-dihydropyran 2 in the present of acid (e.g., sulfuric acid and the like), to give compound 3. Compound 3 is then reacted with magnesium turning in a suitable anhydrous solvent (e.g., tetrahydrofuran and the like). This is followed by reaction with 1-[4-(2-chloroethoxy)phenyl]-2-phenyl-1-butanone 4 to provide compound 5 which, on dehydration/deprotection in presence of acid in a suitable solvent (e.g., methanol and the like), produces compound 6. Reaction of yielded compound 6 with methylamine in a suitable solvent (e.g., isopropanol and the like) provides endoxifen I.

In some embodiments of the present invention, a mixture of E- and Z-isomers of endoxifen can be separated to provide the purified preparations of E- and Z-isomer of endoxifen. The separation of E- and Z-isomers of endoxifen in the present invention can be done, e.g., by crystallization, or purification by liquid column chromatography (LC), or high pressure liquid column chromatography (HPLC).

Suitable solvents that can be employed in present invention for the separation of E- and Z-isomers of endoxifen include but are not limited to hexanes, heptanes, and the like, benzene; toluene; ethyl acetate; acetonitrile; chlorinating solvents such as methylene chloride, chloroform, 1,2-dichloromethane, and the like, ketones, (e.g., acetone, 2-butanone, and the like), ethers such as diethyl ether, diisopropyl ether, methyl butyl ether, and tetrahydrofuran, alcohols such as methanol, ethyl alcohol, and isopropyl alcohol, and the like, and water. A solvent for crystallization can be used as a single solvent, or as mixture of solvents such as hexane-ethyl acetate, chloroform-acetone, chloroform-methanol, dichloromethane-methanol, and the like. When a mixture of two solvents is used in the present invention, examples of ratios of one solvent to another are e.g., in a range such as 9:1 to 1:9, (e.g., 8:2, 7:3; 6:4; 5:5; 4:6; 3:7; 2:8; 1:9, and the like.) However, mixtures for use in the present invention are not limited to these ratios, or to mixtures comprising only two solvents.

Solvents that find use in the preparation of endoxifen according to the present invention include but are not limited to tetrahydrofuran, dichloromethane, chloroform, 1,2-dichloroethane, acetonitrile, N,N'-dimethylformamide, dimethylsulfoxide, toluene, pyridine, methanol, ethanol, isopropanol, acetone, 2-butanone, hexane, heptane, pentane, ethyl acetate, and the like.

Acids that find use in the preparation of endoxifen according to the present invention include, but are not limited to, sulfuric acid, hydrochloric acid, acetic acid, trifluroacetic acid, phosphoric acid, p-toluenesulfonic acid, methanesulfonic acid, nitric acid, and the like.

Intermediates and final products of the present invention can be purified by column chromatography using a single or a mixture of common organic solvents such as hexane pentane, heptane, ethyl acetate, methylene chloride, chloroform, methanol, acetone, and the like.

As noted above, intermediates and final product of the present invention, may, in some embodiments, be purified by crystallization. Solvents that find use in the crystallization of intermediates and products include but are not limited to hydrocarbons such as pentanes, hexanes, heptanes, and the like, benzene; toluene; ethyl acetate; acetonitrile; chlorinating solvents such as methylene chloride, chloroform, 1,2-dichloromethane, and the like; ketones, for example, acetone, 2-butanone, and the like; ethers such as diethyl ether, diisopropyl ether, methyl butyl ether, tetrahydrofuran; alcohols such as methanol, ethyl alcohol, isopropyl alcohol, and the like. A solvent for crystallization can be used as a single solvent or mixture of solvents. Exemplary mixtures include, e.g., hexane-ethyl acetate, chloroform-acetone, chloroform-methanol, dichloromethane-methanol, and the like. When a mixture of two solvents is used in the present invention, examples of ratios of one solvent to another are e.g., in a range such as 9:1 to 1:9, (e.g., 8:2, 7:3; 6:4; 5:5; 4:6; 3:7; 2:8; 1:9, and the like.) However, mixtures for use in the present invention are not limited to these ratios, or to mixtures comprising only two solvents.

One object of the present invention is to provide E-endoxifen or Z-endoxifen with at least 80% purity, such as at least 90% pure or at least 95% pure or at least 98% pure or at least 99% pure or at least 100% pure.

Another object of the present invention is to provide solubilized endoxifen in, e.g., aqueous acid. Suitable acids for solubilizing endoxifen include but are not limited to formic acid, acetic acid, propionic acid, butyric acid, trifluoroacetic acid, lactic acid, tartaric acid, oxalic acid, malonic acid, succinic acid, and the like. The pH of the acidic solution comprising endoxifen can be adjusted with suitable base or buffers. Examples of base and buffers include but are not limited to sodium hydroxide, sodium acetate, sodium lactate, sodium succinate, sodium monophosphate, sodium diphosphate, sodium triphosphate, sodium oxalate, sodium tartarate, ammonium hydroxide, ammonium acetate, and the like. In some embodiments, a co-solvent can also be used to solubilize endoxifen. Examples of co-solvent include but are not limited to ethanol, isopropanol, detergents such as Tween 20 and Polysorbate, and the like In certain preferred embodiments, the pH of a composition containing endoxifen according to the present invention are between about 4.0 and about 8.0, and preferably between about 5.0 and about 8.0, and most preferably between about 5.5 and about 7.5.

In some embodiments, the present invention relates to compositions and methods for delivery of endoxifen or endoxifen-lipid complexes to a mammalian host. Any suitable amount of endoxifen can be used in complex formation. Suitable amounts of endoxifen are those amounts that can be stably incorporated into the complexes of the present invention.

In some embodiments, the inventive composition comprises a lipid complex with endoxifen in which the complex desirably contains lipid or a mixture of lipids. Complexes can be in the form, e.g., of micelles, vesicles or emulsions without exclusion of other forms. The micelles of the present invention can be in the form of monomeric, dimeric, polymeric or mixed micelles. The complexes including micelles and emulsions are predominately in the size range of 50 nm-20 micron, preferably in size range of 50 nm-5 micron. In the complexes, the active agent can be bound to the lipid by covalent, hydrophobic, electrostatic, hydrogen, or other bonds, and is considered bound even where the drug is simply entrapped within the interior of lipid structures.

Endoxifen-lipid complexes may contain e.g., cholesterols or cholesterol derivatives or a mixture of cholesterol and cholesterol derivatives. Cholesterol derivatives that find use in the present invention include cholesteryl hemisuccinate, cholesteryl succinate, cholesteryl oleate, cholesteryl linoleate, cholesteryl eicosapentenoate, cholesteryl linolenate, cholesteryl arachidonate, cholesteryl palmitate, cholesteryl stearate, cholesteryl myristate, polyethylene glycol derivatives of cholesterol (cholesterol-PEG), water soluble cholesterol (for example, cholesterol methyl-β-cyclodextrin), coprostanol, cholestanol, or cholestane, cholic acid, cortisol, corticosterone or hydrocortisone and 7-dehydrocholesterol.

In some preferred embodiments, the compositions also include α-, β-, γ-tocopherols, vitamin E, calciferol, organic acid derivatives of α-, β-, γ-tocopherols, such as α-tocopherol hemisuccinate (THS), α-tocopherol succinate and/or mixtures thereof.

In other some preferred embodiments, endoxifen-lipid complexes of the present invention contain sterols. Sterols that find use in the present invention include β-sitosterol, stigmasterol, stigmastanol, lanosterol, α-spinasterol, lathosterol, campesterol and/or mixtures thereof.

Compositions of the present invention also include endoxifen complexes with free and/or salts or esters of fatty acid. Preferred fatty acids range from those with carbon chain lengths of about $C_2$ to $C_{34}$, preferably between about $C_4$ and about $C_{24}$, and include tetranoic acid ($C_{4:0}$), pentanoic acid ($C_{5:0}$), hexanoic acid ($C_{6:0}$), heptanoic acid ($C_{7:0}$), octanoic acid ($C_{8:0}$), nonanoic acid ($C_{9:0}$), decanoic acid ($C_{10:0}$), undecanoic acid ($C_{11:0}$), dodecanoic acid ($C_{12:0}$), tridecanoic acid ($C_{13:0}$), tetradecanoic (myristic) acid ($C_{14:0}$), pentadecanoic acid ($C_{15:0}$), hexadecanoic (palmatic) acid ($C_{16:0}$), heptadecanoic acid ($C_{17:0}$), octadecanoic (stearic) acid ($C_{18:0}$), nonadecanoic acid ($C_{19:0}$), eicosanoic (arachidic) acid ($C_{20:0}$), heneicosanoic acid ($C_{21:0}$), docosanoic (behenic) acid ($C_{22:0}$), tricosanoic acid ($C_{23:0}$), tetracosanoic acid ($C_{24:0}$), 10-undecenoic acid ($C_{11:1}$), 11-dodecenoic acid ($C_{12:1}$), 12-tridecenoic acid ($C_{13:1}$), myristoleic acid ($C_{14:1}$), 10-pentadecenoic acid ($C_{15:1}$), palmitoleic acid ($C_{16:1}$), oleic acid ($C_{18:1}$), linoleic acid ($C_{18:2}$), linolenic acid ($C_{18:3}$), eicosenoic acid ($C_{20:1}$), eicosdienoic acid ($C_{20:2}$), eicosatrienoic acid ($C_{20:3}$), arachidonic acid (cis-5,8,11,14-eicosatetraenoic acid), and cis-5,8,11,14, 17-eicosapentaenoic acid, among others. Other fatty acids also can be employed in the compositions. Examples of such include saturated fatty acids such as ethanoic (or acetic) acid, propanoic (or propionic) acid, butanoic (or butyric) acid, hexacosanoic (or cerotic) acid, octacosanoic (or montanic) acid, triacontanoic (or melissic) acid, dotriacontanoic (or lacceroic) acid, tetratriacontanoic (or gheddic) acid, pentatriacontanoic (or ceroplastic) acid, and the like; monoethenoic unsaturated fatty acids such as trans-2-butenoic (or crotonic) acid, cis-2-butenoic (or isocrotonoic) acid, 2-hexenoic (or isohydrosorbic) acid, 4-decanoic (or obtusilic) acid, 9-decanoic (or caproleic) acid, 4-dodecenoic (or linderic) acid, 5-dodecenoic (or denticetic) acid, 9-dodecenoic (or lauroleic) acid, 4-tetradecenoic (or tsuzuic) acid, 5-tetradecenoic (or physeteric) acid, 6-octadecenoic (or petroselenic) acid, trans-9-octadecenoic (or elaidic) acid, trans-11-octadecenoic (or vaccinic) acid, 9-eicosenoic (or gadoleic) acid, 11-eicosenoic (or gondoic) acid, 11-docosenoic (or cetoleic) acid, 13-decosenoic (or erucic) acid, 15-tetracosenoic (or nervonic) acid, 17-hexacosenoic (or ximenic) acid, 21-triacontenoic (or lumequeic) acid, and the like; dienoic unsaturated fatty acids such as 2,4-pentadienoic (or β-vinylacrylic) acid, 2,4-hexadienoic (or sorbic) acid, 2,4-decadienoic (or stillingic) acid, 2,4-dodecadienoic acid, 9,12-hexadecadienoic acid, cis-9, cis-12-octadecadienoic (or α-linoleic) acid, trans-9, trans-12-octadecadienoic (or linlolelaidic) acid, trans-10,trans-12-octadecadienoic acid, 11,14-eicosadienoic acid, 13,16-docosadienoic acid, 17,20-hexacosadienoic acid and the like; trienoic unsaturated fatty acids such as 6,10,14-hexadecatrienoic (or hiragonic) acid, 7,10,13-hexadecatrienoic acid, cis-6, cis-9-cis-12-octadecatrienoic (or γ-linoleic) acid, trans-8, trans-10-trans-12-octadecatrienoic (or β-calendic) acid, cis-8, trans-10-cis-12-octadecatrienoic acid, cis-9, cis-12-cis-15-octadecatrienoic (or α-linolenic) acid, trans-9, trans-12-trans-15-octadecatrienoic (or α-linolenelaidic) acid, cis-9, trans-11-trans-13-octadecatrienoic (or α-eleostearic) acid, trans-9, trans-11-trans-13-octadecatrienoic (or β-eleostearic) acid, cis-9, trans-11-cis-13-octadecatrienoic (or punicic) acid, 5,8,11-eicosatrienoic acid, 8,11,14-eicosatrienoic acid and the like; tetraenoic unsaturated fatty acids such as 4,8,11,14-hexadecatetraenoic acid, 6,9,12,15-hexadecatetraenoic acid, 4,8,12, 15-octadecatetraenoic (or moroctic) acid, 6,9,12,15-octadecatetraenoic acid, 9,11,13,15-octadecatetraenoic (or α- or β-parinaric) acid, 9,12,15,18-octadecatetraenoic acid, 4,8, 12,16-eicosatetraenoic acid, 6,10,14,18-eicosatetraenoic acid, 4,7,10,13-docasatetraenoic acid, 7,10,13,16-docosatetraenoic acid, 8,12,16,19-docosatetraenoic acid and the like; penta- and hexa-enoic unsaturated fatty acids such as 4,8, 12,15,18-eicosapentaenoic (or timnodonic) acid, 4,7,10,13, 16-docosapentaenoic acid, 4,8,12,15,19-docosapentaenoic (or clupanodonic) acid, 7,10,13,16,19-docosapentaenoic, 4,7,10,13,16,19-docosahexaenoic acid, 4,8,12,15,18,21-tetracosahexaenoic (or nisinic) acid and the like; branched-chain fatty acids such as 3-methylbutanoic (or isovaleric) acid, 8-methyldodecanoic acid, 10-methylundecanoic (or isolauric) acid, 11-methyldodecanoic (or isoundecylic) acid, 12-methyltridecanoic (or isomyristic) acid, 13-methyltetradecanoic (or isopentadecylic) acid, 14-methylpentadecanoic (or isopalmitic) acid, 15-methylhexadecanoic, 10-methylheptadecanoic, 16-methylheptadecanoic (or isostearic) acid, 18-methylnonadecanoic (or isoarachidic) acid, 20-methylheneicosanoic (or isobehenic) acid, 22-methyltricosanoic (or isolignoceric) acid, 24-methylpentacosanoic (or isocerotic) acid, 26-methylheptacosanoic (or isomonatonic) acid, 2,4,6-trimethyloctacosanoic (or mycoceranic or mycoserosic) acid, 2-methyl-cis-2-butenoic(angelic)acid, 2-methyl-trans-2-butenoic (or tiglic) acid, 4-methyl-3-pentenoic (or pyroterebic) acid and the like.

In some preferred embodiments, endoxifen-lipid complexes contain phospholipids. Any suitable phospholipids or mixture of phospholipids can be used. For example, phospholipids can be obtained from natural sources or chemically synthesized. Suitable phospholipids include but are not limited to phosphatidylethanolamine (PE), phosphatidylglycerol (PG), phosphatidylserine (PS), phosphatidylcholine (PC), phosphatidylinositol (PI), phosphatidic acid (PA), sphingomyelin and the like, either used separately or in combination. Phosphatidylglycerols may be having short chain or long chain, saturated or unsaturated such as dimyristoylphosphatidylglycerol, dioleoylphosphatidylglycerol, distearoylphosphatidylglycerol, dipalmitoylphosphatidylglycerol, diarachidonoylphosphatidylglycerol, short chain phosphatidylglycerol ($C_6$-$C_8$), and mixtures thereof. Examples of phosphatidylcholines includes dimyristoylphosphatidylcholine, distearoylphosphatidylcholine, dipalmitoylphosphatidylcholine, dioleoylphosphatidylcholine, diarachidonoylphosphatidylcholine, egg phosphatidylcholine, soy phosphatidylcholine or hydrogenated soy phosphatidylcholine can be used, as can mixtures thereof.

According to one aspect, the present invention provides compositions comprising endoxifen and derivatives of mono-, di- and tri-glycerides. Examples of the glycerides include 1-oleoyl-glycerol (monoolein) and 1,2-dioctanoyl-sn-glycerol.

Another aspect of the invention provides forming complexes of endoxifen with functionalized phospholipids including but not limited to phosphatidylethanolamine, preferably dioleoylphosphatidylethanolamine, phosphatidylthioethanol, N-biotinylphosphatidylethanolamine and phosphatidylethylene glycol.

Another aspect of the invention provides forming complexes of endoxifen with carbohydrate-based lipids. Examples of carbohydrate-based lipids include but are not limited to galactolipids, mannolipids, galactolecithin and the like.

In other preferred embodiment, endoxifen-lipid complexes comprise sterols. Sterols finding use in the present invention include but are not limited to β-sitosterol, stigmasterol, stigmastanol, lanosterol, α-spinasterol, lathosterol, campesterol and/or mixtures thereof.

Another aspect of the invention provides forming complexes of endoxifen with guggulipid and any suitable phospholipids. Guggulipid, or guggul, is a natural substance derived from the mukul myrrh tree. The mukul myrrh gives off a sticky resin, which is processed to obtain guggulipid. This extract has been used for thousands of years in Aryuvedic medicine to treat arthritis and obesity. The guggulipid is a source of sterol compounds such as Z- and E-guggulsterones, generally present in an amount of at least 2.5% (10). Z and E-Guggulsterones can be synthesized chemically and thus can be used in drug formulations where the need is to have pure forms of these sterones. See, e.g., U.S. Application Ser. No. 60/856,952, filed Nov. 6, 2006, and PCT/US07/83832, filed Nov. 6, 2007, both incorporated herein by reference.

Yet another aspect of the invention provides forming complexes of endoxifen with derivatives of phospholipids such as pegylated phospholipids. Examples of pegylated lipids finding use in the present invention include but are not limited to the polyethylene glycol (Pegylated, PEG) derivatives of distearoylphosphatidylglycerol, dimyristoylphosphatidylglycerol, dioleoylphosphatidylglycerol and the like.

In other aspects, the present invention provides compositions comprising endoxifen and polyethyleneglycol (PEG) and one or more lipids.

According to yet other aspects, the present invention provides compositions comprising endoxifen complexes with one or more lipids. Examples include but are not limited to compositions comprising endoxifen, cholesterol or cholesterol derivatives and one or more phospholipids. Other examples of compositions include endoxifen, β-sitosterol, and one or more phospholipids. In some preferred embodiments, compositions of the present invention comprise endoxifen, and hydrogenated soy phosphatidylcholine or soy phosphatidylcholine.

The term "Polyethylene glycol (PEG)" includes polymers of lower alkylene oxide, in particular ethylene oxide (polyethylene glycols) having an esterifiable hydroxyl group at least at one end of the polymer molecule, as well as derivatives of such polymers having esterifiable carboxy groups. Polyethylene glycols of an average molecular weight ranging from 200-20,000 are preferred; those having an average molecular weight ranging from 500-2000 are particularly preferred.

Another aspect of the invention provides forming complexes of endoxifen with carbohydrate-based lipids. Examples of carbohydrate-based lipids include but are not limited to galactolipids, mannolipids, galactolecithin and the like.

In some embodiments of compositions of the invention, a complex is formed comprising endoxifen and preferably endoxifen in water at a concentration of about 0.5 mg/mL to about 25 mg/mL, such as between 1 mg/mL and about 20 mg/mL or between 1 mg/mL and 10 mg/mL, more preferably between 1 mg/mL and 5 mg/mL.

In some embodiments, compositions of the present invention contain about 2.5% to about 90% of total lipid, preferably about 2.5 to about 50% weight of total lipid or more, preferably about 10% to about 50% weight of total lipid.

In certain embodiments, compositions of the present invention preferably contain endoxifen, and lipid(s) in mole ratio between 1:1 to 1:100 such as in between 1:1 and 1:20 molar ratio or in between 1:1 and 1:30 molar ratio or in between 1:1 and 1:40 molar ratio or in between 1:1 and 1:50 molar ratio, in between 1:1 and 1:60 molar ratio, in between 1:1 and 1:70 molar ratios, and in between 1:1 and 1:80 molar ratios, and 1:90 molar ratios.

Ratios recited herein, e.g., mole ratios of components in a composition, are provided by way of example and do not limit the invention to the precise incremental ratios recited, e.g., to whole number ratios of the components in the composition. For example, a range of ratios of about 1:10 to 1:90 encompasses not only 1:11, 1:25, 1:89, etc., but includes, without limitation, any ratio at or between about 1:10 to 1:90 (e.g., 1:53.637).

In certain embodiments, compositions of the present invention preferably contain endoxifen and hydrogenated soy phosphatidylcholine, or soy phosphatidylcholine, and cholesterol or cholesterol derivative. Such composition includes endoxifen and cholesterol or cholesterol derivative preferably in from about 1:1-1:5 mole ratio, and more preferably at about 1:1 mole ratio to about 1:2 mole ratio.

Yet another aspect of the invention is to form complexes of endoxifen with derivatives of phospholipids, such as pegylated phospholipids. Examples include but are not limited to the polyethylene glycol (PEG) derivatives of distearoylphosphatidylglycerol, dimyristoylphosphatidylglycerol, dioleoylphosphatidylglycerol and the like.

In some preferred embodiments, the mole ratio of endoxifen and hydrogenated soy phosphatidylcholine or soy phosphatidylcholine, in a composition containing endoxifen and hydrogenated soy phosphatidylcholine or phosphatidylcholine is between about 1:10 and 1:90, e.g., between about 1:10 and 1:80 or 1:10 and 1:70 or 1:10 and 1:60 or 1:10 and 1:50 or 1:10 and 1:40 and 1:10 and 1:30. Particularly preferred embodiments, the mole ratio of endoxifen and hydrogenated soy phosphatidylcholine or soy phosphatidylcholine is between 1:10 and 1:60.

In some embodiments, compositions of the present invention preferably contain endoxifen and total lipids having weight to weight ratio between 1:1 to 1:100 ratio such as between 1:1 and 1:20 ratio or between 1:1 and 1:30 ratio or between 1:1 and 1:40 ratio or between 1:1 and 1:50 ratio, or between 1:1 and 1:60 ratio, or between 1:1 and 1:70 ratio, and between 1:1 and 1:80 ratio, or in between 1:1 and 1:90 ratio.

In some embodiments, the method of the present invention comprises solubilizing or suspending endoxifen and lipid(s) together in an aqueous solution, e.g., water. Endoxifen-lipid complex solution can be filtered through suitable filters to control the size distribution of the complexes.

In some embodiments, the method may comprise mixing lipid(s) together in water and then adding endoxifen. Endoxifen-lipid complex solution can be filtered through suitable filters to control the size distribution of the complexes.

In some embodiments, the method also comprises mixing endoxifen and lipid(s) in an organic solvent(s), such as chloroform or ethanol or any other pharmaceutically acceptable solvents, and evaporating the solvent(s) to form a lipid phase or lipid film. The lipid phase is then hydrated with water or an aqueous solution. Examples of aqueous solutions include but are not limited to 0.9% sodium chloride, solutions containing sugars such as dextrose, sucrose, and the like. The hydrated solution can be filtered through suitable filters to control the size distribution of the complexes.

In some embodiments, the method comprises mixing lipid(s) in an organic solvent(s) and evaporating the solvent(s) to form a lipid phase or lipid film. The lipid phase is then hydrated with aqueous solution containing endoxifen. The aqueous solution in addition to endoxifen may further contain sodium chloride or sugars such as dextrose, sucrose and the like. The hydrated solution can be filtered through suitable filters to control the size distribution of the complexes.

In other embodiments, the method of the present invention comprises mixing endoxifen, one or more lipids in any suitable order and in any suitable solvents such that the resulting composition of the present invention contains endoxifen, and one or more lipids.

In some embodiments, the method of preparation of the present invention comprises heating the composition comprising endoxifen, and the lipid(s) at temperatures ranging from 30-100° C. preferably between 30-80° C. and more preferably between 30-60° C.

In some embodiments, the pH of the composition of invention ranges from about 3 to about 11, while a pH between 3.5 to about 8 is preferred and pH of between 4.0 to pH 7.5 are particularly preferred. Aqueous solutions having of a particular pH can be prepared from water having comprising appropriate buffers. Preferred buffers include but are not limited to mixtures of monobasic sodium phosphate and dibasic sodium phosphate, tribasic sodium phosphate, disodium succinate. Other buffers that find use with the present invention include sodium carbonate, sodium bicarbonate, sodium hydroxide, ammonium acetate, sodium citrate, tris (hydroxy-methyl) aminoethane, sodium benzoate, and the like.

The mole ratio of endoxifen and hydrogenated soy phosphatidylcholine or soy phosphatidylcholine in the composition containing endoxifen and hydrogenated soy phosphatidylcholine or soy phosphatidylcholine is in between 1:10 and 1:90 such as in between 1:10 and 1:80 or 1:10 and 1:80 or 1:10 and 1:60 or 1:10 and 1:50 or 1:10 and 1:40 and 1:10 and 1:30. In preferred embodiments, the mole ratio of endoxifen and hydrogenated soy phosphatidylcholine or soy phosphatidylcholine is in between 1:5 and 1:60.

As noted above, compositions can be filtered to obtain a desired size range of complexes particle sizes from the filtrate. Filters that find use in the present invention include those that can be used to obtain the desired size range of the complexes from the filtrate. For example, the complexes can be formed and thereafter filtered through a 5 micron filter to obtain complexes, each particle having a diameter of about 5 micron or less. Alternatively, 1 μm, 500 nm, 200 nm, 100 nm or other filters can be used to obtain complexes having diameters of about 1 μm, 500 nm, 200 nm, 100 nm or any suitable size range, respectively.

When desired, the endoxifen-lipid complex can be dried, e.g., by evaporation or lyophilization. In certain embodiments of the invention, the endoxifen-lipid complex can be lyophilized with one or more cryoprotectants such as sugars. In preferred embodiments, sugars include but are not limited to trehalose, maltose, lactose, sucrose, glucose, and dextran. In particularly preferred embodiments, trehalose and/or sucrose are used. Lyophilization is accomplished under vacuum and can take place either with or without prior freezing of the endoxifen lipid preparation. When desired, the complexes can be resuspended in any desirable solvent including water, saline, dextrose and buffer.

Pharmaceutical preparations that find use with the compositions of the present invention include but are not limited to tablets, capsules, pills, dragees, suppositories, solutions, suspensions, emulsions, ointments, and gels. For the oral mode of administration, preferred forms of endoxifen or endoxifen lipid complex include tablets, capsules, lozenges, powders, syrups, aqueous solutions, suspensions and the like. For topical application and suppositories, preferred forms of endoxifen or endoxifen-lipid complex comprise gels, oils, and emulsions, such as are formed by the addition of suitable water-soluble or water-insoluble excipients, for example polyethylene glycols, certain fats, and esters, compounds having a higher content of polyunsaturated fatty acids and derivatives thereof. Derivatives include mono-, di-, and triglycerides and their aliphatic esters (for example, fish oils, vegetable oils etc.) or mixtures of these substances. Suitable excipients are those in which the drug complexes are sufficiently stable to allow for therapeutic use.

When desired, composition containing endoxifen or endoxifen-lipid complex can be encapsulated in enteric-coated capsules to protect it from acids in the stomach. The term "enteric" refers to the small intestine, and enteric coatings prevent release of medication before it reaches the small intestine. Most enteric coatings work by presenting a surface that is stable at acidic pH but breaks down rapidly at higher pH. Enteric coating of capsules filled with composition containing endoxifen or endoxifen-lipid complex can be done as methods known in the art.

The endoxifen-lipid complex of the present invention can be of varying size or can be of substantially uniform size. For example, the complex can have a mean diameter of about 1 mm or less, and more preferably are in the micron or sub-micron range. In some preferred embodiments, the complexes have an average diameter of about 5 μm or less, such as 0.2 μm or less or 0.1 μm or less.

The technology outlined in the present invention may also be used for any other water-insoluble drugs. The methods and compositions of the present invention find use in conjunction with the methods and compositions disclosed in U.S. Application Ser. No. 60/850,446, filed Oct. 10, 2006, PCT Application Ser. No. PCT/US07/80984, filed Oct. 10, 2007, U.S. Application Ser. No. 60/856,952, filed Nov. 6, 2006, PCT Application Ser. No. PCT/US07/83832, filed Nov. 6, 2007, all of which are incorporated by reference herein in their entireties.

The compositions of the present invention can be employed to treat breast cancer and breast related diseases. For example, the compositions of the present invention may be administered to a patient diagnosed with benign breast disease. As used herein, the term "benign breast disease" refers to a constellation of non-malignant aberrations in breast tissue. The aberrations may be proliferative or non-proliferative in nature. The exemplary benign breast diseases treatable by the present inventive compositions include adenosis, cysts, duct ectasia, fibroadenoma, fibrosis, hyperplasia, metaplasia and other fibrocystic changes. Each of these diseases, referred as "changes" or "conditions" due to their prevalence, have well-defined histological and clinical characteristics.

"Adenosis" refers to generalized glandular disease of the breast. It typically involves an enlargement of breast lobules, which contain more glands than usual. In "sclerosing adenosis," or "fibrosing adenosis," the enlarged lobules are distorted by scar-like fibrous tissue.

"Cysts" are abnormal sacs filled with fluid or semi-solid material. Cysts in the breast are lined by breast epithelial cells, developing from lobular structures. They begin as excess fluid inside breast glands, but may grow to proportions that stretch surrounding breast tissue, causing pain. "Fibrocysts" are cystic lesions circumscribed by, or situated within, a conspicuous amount of fibrous connective tissue.

"Duct ectasia" refers to a dilation of mammary ducts by lipid and cellular debris. Rupture of the ducts induces infiltration by granulocytes and plasma cells.

"Fibroadenoma" refers to benign tumors that are derived from glandular epithelium and contain a conspicuous stroma of proliferating fibroblasts and connective tissue.

"Fibrosis" simply refers to a prominence of fibrous tissue in the breast.

"Hyperplasia" refers to an overgrowth of cells, where several layers of cells line the basal membrane, without tumor formation. Hyperplasia increases the bulk of mammary tissue. In "epithelial hyperplasia," the cells lining breast ducts and lobules are involved, giving rise to the terms "ductal hyperplasia" and "lobular hyperplasia." Based on a histological determination, hyperplasia may be characterized as "usual" or "atypical".

"Metaplasia" refers to a phenomenon in which a differentiated tissue of one type transforms into a differentiated tissue of another type. Metaplasia often results from an environmental change, and enables cells better to withstand the change.

The compositions of the present invention may be administered in any dosage form and via any system that delivers the active compound endoxifen to breast estrogen receptors in vivo. In some embodiments, a composition of present invention is delivered by "percutaneous administration", e.g., delivering the drug from the surface of patient's skin, through the stratum corneum, epidermis, and dermis layers, and into the microcirculations. This is generally accomplished by diffusion down a concentration gradient. The diffusion may occur via intracellular penetration (through the cells), intercellular penetration (between the cells), transappendageal penetration (through the hair follicles, sweat, and sebaceous glands), or any combination of the above.

Percutaneous administration of the endoxifen composition of the present invention may be advantageous because this may reduce systemic drug exposure and the risks from non-specifically activating estrogen receptors throughout the body. This is because in topical application of endoxifen will absorb primarily into local tissues. When the composition of invention containing endoxifen will be percutaneously applied to breasts, high concentration will accumulate in the breast tissues presumably due to many estrogen receptors therein. The composition of endoxifen may be applied to any skin surface, preferably to one or both breasts. The daily doses to be administered can initially be estimated based upon the absorption coefficients of endoxifen, the breast tissue concentration that is desired, and the plasma concentration that should not be exceeded. The initial dose may be optimized in each patient, depending on individual responses.

Percutaneous administration can be achieved in different ways, such as (i) by mixing the composition of endoxifen with suitable pharmaceutical carriers and, optionally, penetration enhancers to form ointments, emulsions, gel, lotion, creams or the like, where an amount of said preparation is applied onto a certain area of the skin, (ii) by incorporating the composition of endoxifen into patches or transdermal delivery systems according to the technology known in the art.

The effectiveness of percutaneous drug administration depends on many factors, such as drug concentration, surface area of application, time and duration of application, skin temperature, skin hydration, previous irradiation, physicochemical properties of the drug, and partitioning of the drug between the formulation and the skin. In some embodiments, e.g., to enhance percutaneous effectiveness, the compositions or complexes comprise penetration enhancers that improve percutaneous absorption by reducing the resistance of stratum corneum by reversibly altering its physicochemical properties, changing hydration in the stratum corneum, acting as co-solvent, or changing the organization of lipids or proteins in the intracellular spaces. Such enhancers include but are not limited to organic solvents such as alcohol, acetone, dimethylsulfoxide (DMSO), polyethylene glycol, propoylene glycol, fatty acids and fatty alcohol and their derivatives, hydroxyl acids, pyrrolidones, urea, vegetable oils, essential oils, and mixture thereof. In addition to chemical enhancers, physical methods can increase percutaneous absorption. For example, occlusive bandages induce hydration of the skin. Other physical methods include iontophoresis and sonophoresis, which use electrical fields and high-frequency ultrasound, respectively, to enhance absorption of drugs that are poorly absorbed due to their size and ionic characteristics (12-13). Those who are in the pharmaceutical field can easily manipulate the various factors and methods to achieve right efficacious dosage for percutaneous delivery.

For percutaneous administration, the formulation or composition of the invention containing endoxifen may be delivered in the form of ointment, emulsion (lotion), cream, gel, powder, oil or similar formulation. In some embodiments, the formulation comprises excipient additives, including but not limited to vegetable oils such as soybean oil, mustard oil, almond oil, olive oil, groundnut oil, peanut oil, peach kernel oil, groundnut oil, castor oil, canola oil, and the like, animal fats, DMSO, lanolin lipoids, phosphatides, hydrocarbons such as paraffin's, petroleum jelly, waxes, lecithin, detergent emulsifying agents, carotin, alcohols, glycerol, glycerol ether, glycerine, glycol, glycol ethers, polyethylene glycol, polypropylene glycol, non-volatile fatty alcohols, acids, esters, volatile alcoholic compounds, talc, urea, cellulose derivatives, coloring agents, antioxidants and preservatives.

In some embodiments the formulation or composition of the invention containing endoxifen may be delivered as transdermal patch. The patch may comprise (i) a solution-impermeable backing foil, (ii) a layer like element having a cavity, (iii) a microporous or semipermeable membrane, (iv) a self-adhesive layer, and (v) optionally a removable backing film. The layer-like element having a cavity may be formed by the backing foil and the membrane. Alternatively, the patch may comprise (i) a solution-impermeable backing foil. (ii) an open-pored foam, a closed pore foam, a tissue like layer or a fibrous web-like layer as reservoir, (iii) a self adhesive layer, and (iv) optionally a removable backing film.

In some preferred embodiments, the composition of the invention containing endoxifen is formulated in hydro alcoholic gel and the amount of endoxifen may vary from 0.001001 to 1.0 gram per 100 grams of gel, most preferably in the range of 0.01-0.20 grams per 100 grams of gel.

In other embodiments, the composition of present invention comprises one or more fatty acid esters as a penetration enhancer. One of the highly preferred examples of a fatty acid ester penetration enhancer is isopropyl myristate. When isopropyl myristate is used in gel, the amount may range e.g., from 0.11 to 5.0 grams per 100 grams of gel, preferably from 0.5 to 2.0 grams per 100 grams of gel.

In another preferred embodiment the composition of invention containing endoxifen may also contain one or more nonaqueous vehicles, such as alcoholic vehicles. Examples of nonaqueous vehicles include ethyl acetate, ethanol, and isopropanol, preferably ethanol and isopropanol. These nonaqueous vehicles may be useful for dissolving both the active agent endoxifen and any other penetration enhancer used. They also preferably have a low boiling point, preferably less than 100° C. at atmospheric pressure, to permit rapid evaporation upon contact with skin. In particular, ethanol may effectively contribute to the percutaneous absorption of endoxifen by rapidly evaporating upon contact with skin. The amount of absolute nonaqueous vehicle in a gel formulation ranges from 35% to 99% by weight, preferably between 50% to 85% and more preferably between 60% to 75%.

In another preferred embodiment, the composition or formulation of the invention comprises an aqueous vehicle that permits solubilization of hydrophilic molecules, and promotes moisturization of skin. An aqueous vehicle also can regulate pH. Aqueous vehicles include alkalinizing and basic buffer solutions, including phosphate buffer solutions, including phosphate buffer solutions (e.g., dibasic or monobasic sodium phosphate); citrate buffered solutions (e.g., sodium citrate or potassium citrate) and purified water. The amount of an aqueous vehicle preferably ranges between 0.1% to 65% by weight of the pharmaceutical composition, preferably between 15% to 50%, and more preferably between 25% to 40%.

In other embodiments, the composition of the invention comprises one or more gelling agents to increase the viscosity of the composition or formulation or to function as a solubilizing agent. It may constitute between 0.1% to 20% by weight of formulation depending on the nature of gelling agent, preferably between 0.5% to 10% and more preferably between 0.5% to 5%. The gelling agents may be carbomers, cellulose derivatives, poloxamers and poloxamines. The preferred gelling agents are chitosan, dextran, pectins, natural gums and cellulose derivatives such as ethyl cellulose, hydroxyethyl cellulose, hydroxypropyl cellulose, hydroxypropyl methyl cellulose (HPMC), carboxymethyl cellulose (CMC) and the like. The most preferred gelling agent is hydroxypropyl cellulose.

The composition of invention may comprise a gelling agent as described above, in particular a non-preneutralized acrylic polymer and also comprise a neutralizing agent. The ratio of neutralizing agent/gelling agent varies in between 10:1 to 0.1:1, preferably between 7:1 to 0.5:1, and more preferably between 4:1 to 1:1. A neutralizing agent in the presence of polymer should form salts that are soluble in the vehicle. A neutralizing agent also should permit optimum swelling of polymer chains during neutralization of charges and formation of polymer salts. The neutralizing agents include ammonium hydroxide, potassium hydroxide, sodium hydroxide, aminomethylpropanol, trolamine, and tromethamine. Those skilled in the art will select a neutralizing agent according to the type of geling agent used in the composition or formulation. However, no neutralizing agent is required when a cellulose derivative will be used as geling agents.

In some embodiments, the compositions of present invention are employed to treat other diseases, and the medication is selected from a lipophilic or a compound made lipophilic by derivatization of the group consisting of antiasthama, antiarrhythmic, antifungals, antihypertensive, anticancer, antibiotics, antidiabetics, antihistamines, antiparasitics, antivirals, cardiac glycosides, hormones, immunotherapies, antihypotensives, steroids, sedatives and analgesics, tranquilizers, vaccines, and cell surface receptor blockers.

All references, including publications, patent applications, and patent cited herein, including those in the list below and otherwise cited in this specification, are hereby incorporated by reference to the same extent as if each reference was individually and specifically indicated to be incorporated by reference and were set forth in the entirely herein.

The use of terms "a" and "an" and "the" and similar referents in the context of describing the invention (especially in the context of the following claims) are to be construed to cover both the singular and the plural, unless otherwise indicated herein or clearly contradicted by context. The terms "comprising", "including", "having", and "containing" are to be construed as open-ended terms (i.e. meaning "including but not limited to") unless otherwise noted. The use of any and all examples, or exemplary language (e.g., "such as") provided herein, is intended merely to better illuminate the invention and does not pose a limitation on the scope of the invention unless otherwise claimed. No language in the specifications should be constructed as indicating any non-claimed element as essential to the practice of the invention.

Preferred embodiments of this invention are described, including the best mode known to the inventors for carrying out the invention. Variations of those preferred embodiments can become apparent to those of ordinary skilled artisans to employ such variations as appropriate, and the inventors intend for the inventions to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

The following examples further illustrate the invention and are not to be construed as in any way as limiting its scope.

Example 1

Synthesis of Compound 3

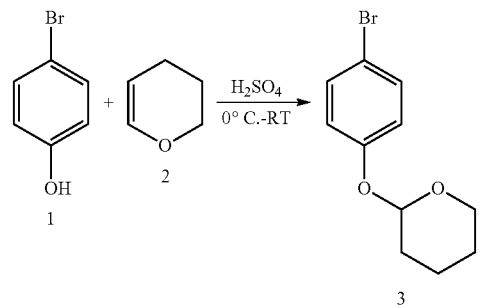

4-Bromophenol (1, 1 kg) and 3,4-dihydro-2H-pyran (2, 1.5 L) was mixed together in a round bottom flask and cooled to 0° C. Conc. Sulfuric acid (1 mL) was added drop wise while maintaining the temperature below room temperature. The solution was stirred at RT for 1 hr. The reaction solution was diluted with hexane and washed with water (1 L) followed by 5% sodium bicarbonate solution (1 L). The organic layer was dried over sodium sulfate, filtered and evaporated in vacuo at 50-55° C. to give an oil (1.55 Kg). Hexane (300 mL) was added to the oil and triturated to give white solid 3. The suspension was cooled to 0° C. and stirred for 30 min before it was filtered and washed with cold hexane (100 mL) and dried. Yield 1.32 Kg.

Example 2

Synthesis of Compound 5

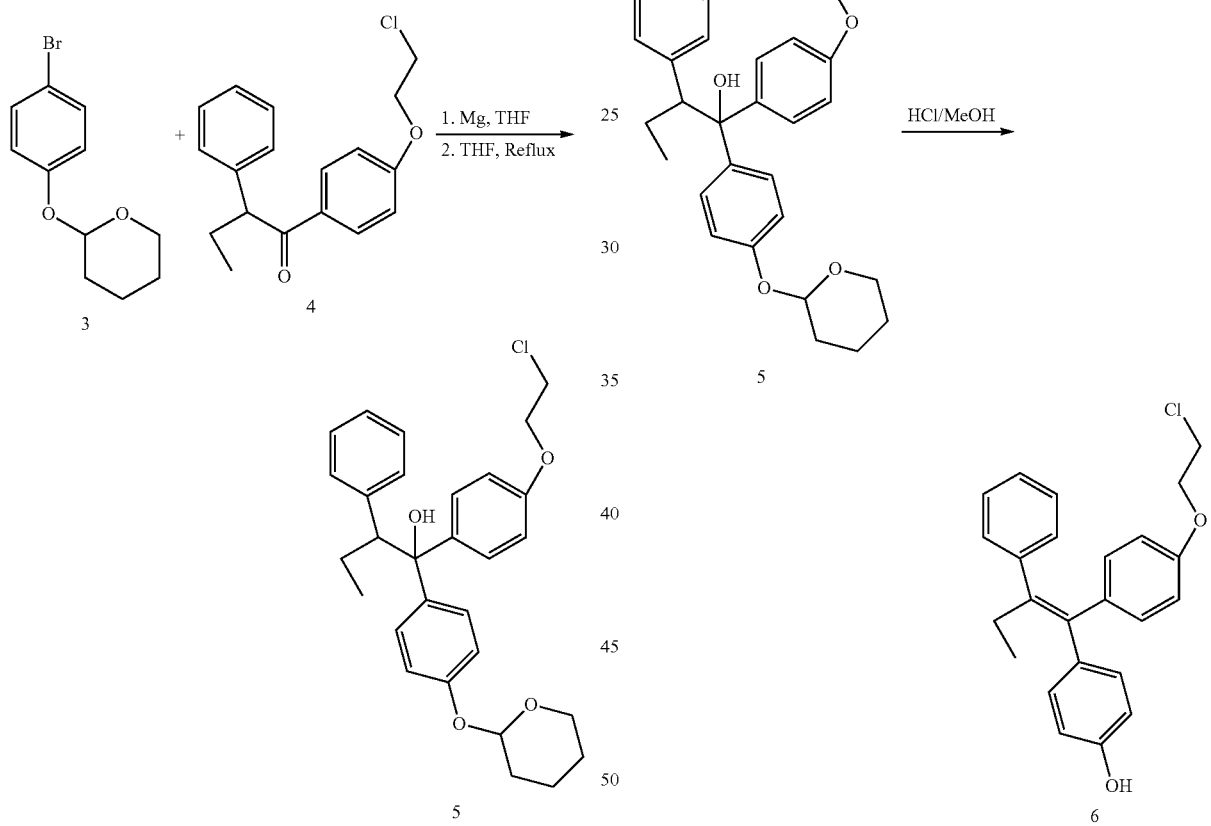

Magnesium turnings (115 g) were added to a 10_L 4-neck round bottom flask containing anhydrous tetrahydrofuran (1 L). The mixture was heated to 55° C. Iodine chips (approx. 5) were added in one lot followed by ethyl bromide (5 mL). Compound 3 (1.1 kg) was dissolved in THF (2 L). 200 mL of this solution was added at once to Mg-THF suspension. The reaction was initiated after 30 mins and reflux started. Remaining solution of compound 3 was added drop wise maintaining the reflux temperature over a period of 1.5 h. The reaction mixture was further refluxed for 2 hr and the cooled to RT. (2-Chloroethoxyphenyl) phenyl butanone (4, 870 g) in THF (1.5 L) was added drop wise over a period of 1 h maintaining the temperature between 30-35° C. The reaction mixture was refluxed for 4 h and cooled to RT. The reaction mixture was poured into ice cold 50% hydrochloric acid (3 L). The organic layer was separated and the aqueous layer was extracted with THF (3×500 mL). The organic layers were combined, dried over sodium sulfate, filtered and concentrated to give 5 as oil which was carried over to next step without further purification. Yield—1.57 kg.

Example 3

Synthesis of Compound 6

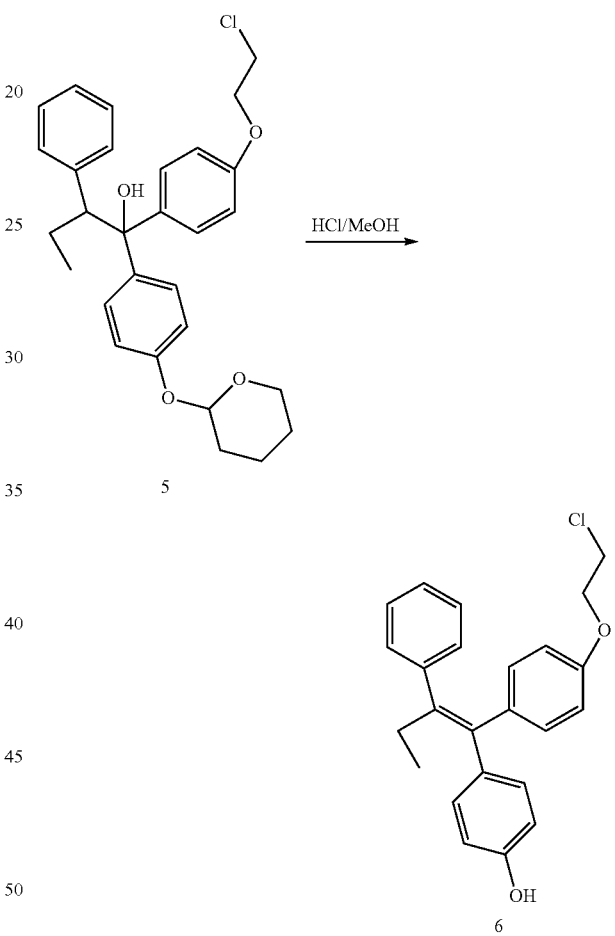

Compound (5, 1.57 kg) was dissolved in methanol (6 L) and conc. hydrochloric acid (1.57 kg) was added. The solution was refluxed for 5 h. Methanol was removed in vacuo and dichloromethane (5 L) was added. The organic layer was separated. The aqueous layer was extracted with dichloromethane (2×500 mL). The organic layers were combined and washed with water (2 L), 5% aq. NaHCO3 (2 L), water (2 L), dried over sodium sulfate. Charcoal was added and filtered. The solvent was removed under vacuum to give oil (1.38 kg). The oil was triturated with hexane (5 L) with vigorous stirring to yield 6 as solid product which was filtered and dried. Yield 1.07 kg.

Example 4

Synthesis of Compound I

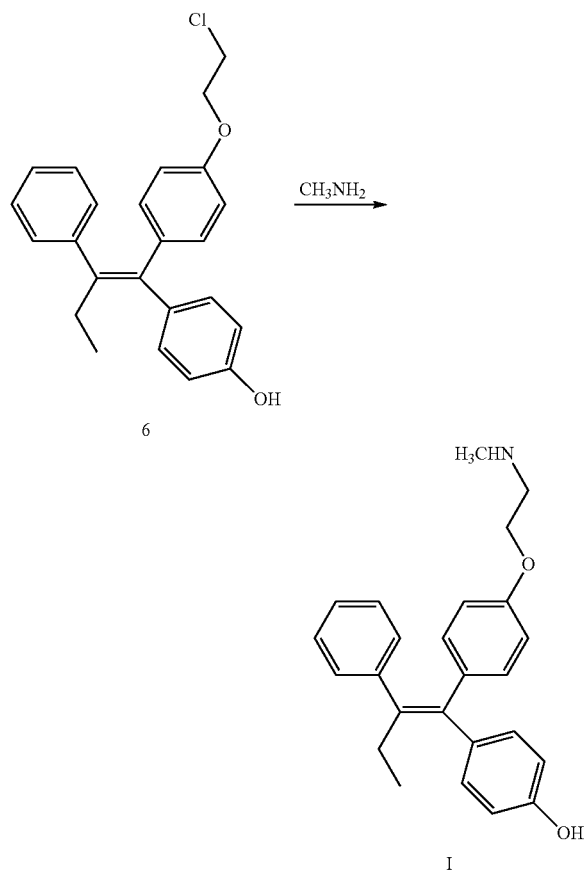

To a solution of compound 6 (50 g) in isopropanol (500 mL), monomethyl amine (300 mL) was added and heated for 24 h maintaining the temperature between 70-75° C. The completion of reaction was monitored by TLC (toluene:triethylamine, 7:3). The solvent was removed in vacuo. Water (500 mL) was added to the residue and extracted with diisopropyl ether (DIPE, 500 mL). The organic layer was separated and the aqueous layer was back extracted with DIPE (200 mL). The organic layers were combined and washed with water (500 mL), 5% aq. sodium bicarbonate (500 mL), dried over sodium sulfate and filtered. The solvent was removed in vacuo to give a gummy residue. Ethyl acetate (50 mL) was added and heated to dissolve the residue completely. The solution was cooled to RT and hexane (50 mL) was added and stirred for 12 h. The solid was filtered and washed with cold ethyl acetate-hexane (1:1, 10 mL) mixture. Product 1 was dried overnight under high vacuum. Yield 25 g.

Example 5

Endoxifen Solution

Endoxifen solution (1 mg/mL) was prepared by solubilizing endoxifen (10.3 mg) in 0.2% glacial acetic acid (10 mL). The pH (~5.75) of the solution was adjusted with 1N sodium hydroxide (300 μL).

Example 6

Endoxifen Solution

Endoxifen solution (5 mg/mL) was prepared by solubilizing endoxifen (100 mg) in 2% glacial acetic acid (8.6 mL). The solution was diluted with 5% dextrose (10.97 mL). The pH (~5.56) of the solution was adjusted with 5N sodium hydroxide (430 μL).

Example 7

Endoxifen Complexes

A suspension of endoxifen, cholesteryl sulfate, and soy lecithin, is produced by mixing the components together in water and homogenizing using. e.g., a high pressure homogenizer. The resulting suspension can be filtered through 0.2 μm filter and then mixed with 7.5% sucrose solution and lyophilized in either vials or in bulk. The particle size of the resulting complexes is determined using standard procedures, e.g., using a Nicomp particle sizer 380.

Example 8

Endoxifen Complexes

A suspension of endoxifen and soy lecithin is produced by mixing the components together in water and homogenizing using, e.g., a high pressure homogenizer. The resulting suspension can be filtered through 0.2 μm filter and then mixed with 7.5% sucrose solution and lyophilized in either vials or in bulk. The particle size is determined using standard procedures, e.g., using a Nicomp particle sizer 380.

Example 9

Toxicity Testing

Endoxifen was formulated according to Example 6 and was tested for toxicity in male Balb/c mice. A single test dose at 100 mg/kg or 50 mg/kg was intravenously administered to mice. All the mice died at the 100 mg/kg dose level whereas all animals survived at the 50 mg/kg dose level with no significant loss of body weight. The mice also survived in the control group with a vehicle control that lacked endoxifen. Repeat dose toxicity study was conducted with a dose of 25 mg/kg administered consecutively for 3 days with accumulated dose of 75 mg/kg. All the animals in this group survived. The results are reported in the table below as the number of mice surviving per total.

| Treatment | Dose (mg/kg) | Survival/Total |
| --- | --- | --- |
| Single dose | 100 | 0/2 |
|  | 50 | 4/4 |
| Repeat dose | 25 | 4/4 |

Example 10

Endoxifen Exhibits Anti-Proliferative Activity Against Different Tumor Cells Endoxifen was tested for antiproliferation activity against various cancer cell lines from Non Small Lung Cancer, Breast Cancer, Prostate Cancer, Melanoma Cancer, Ovarian Cancer, CNS Cancer, Renal Cancer and Colon Cancers. The cells were incubated for multiple days (3-7) with Endoxifen (10 nM to 10 μM) and the inhibition of growth were measured by SRB or MTT staining method. The results indicated significant growth inhibition of cells in the presence of Endoxifen ranging from 10 to 100%. Endoxifen induce growth inhibition or cell killing in different tumor cells indicates the usefulness of Endoxifen in the treatment of cancers in humans.

Example 11

Endoxifen Inhibits Estradiol Dependent Breast Tumor Growth

It is known that Tamoxifen antagonizes estradiol-dependent breast cancer xenograft growth (15). Endoxifen base and endoxifen-citrate in oral dosage form can be similarly be tested for inhibition of estradiol dependent MCF-7 xenograft growth. For the animal experiments, female nude mice (Bom: NMRI-nu/nu) per xenograft experiment, ages 4 to 6 weeks and weighing 20 to 24 g, are used according to standard protocols. An example of such a procedure is as follows:

MCF-7 xenografts are developed by passage of transplantable tumor from a parent tumor established in oophorectomized athymic nude mice treated with estradiol (16-17).

Randomly bred female athymic mice are bilaterally ovriectomized and allowed a 2-week recovery period before the implantation of tumor material. The s.c. transplantation of the MCF-7 tumor fragments (size, 1×1×1 mm$^3$) is done under anesthesia. The diameter of the tumors is measured regularly, e.g., once weekly, using a caliper-like mechanical instrument and the tumor volume (V) is calculated according to the empirical equation V=(length×width$^2$)/2. The median volumes of each group are normalized to the initial tumor volume resulting in the relative tumor volume. In all the experiments, tumor-bearing mice receive estradiol supplementation [estradiol valeriate (E2D), 0.5 mg/kg once/wk i.m.]. This supplementation leads to physiologic levels of serum E2 (25-984 pg/mL) that are comparable to the human situation (25-600 pg/mL depending on the follicular phase).

Substances: The following substances are used: E2D, Tamoxifen and endoxifen.

Treatment Modalities: All MCF-7 transplanted animals receive E2D (0.5 mg/kg) injections once a week. After 4 weeks, when hormone-supplemented tumors have grown to ~0.7-0.8 cm in diameter (180-250 mm$^3$), the mice are randomized into 4 treatment groups of 5-10 mice each. The 5-10 mice are sacrificed as baseline controls for E2D alone.

The treatment groups are: (i) E2D support (0.5 mg/kg once/wk i.m); (ii) E2D support (0.5 mg/kg once/wk i.m) plus Tamoxifen (0.5 mg-2 mg)/mouse per day, 5 days/week by gavage; (iii) E2D support (0.5 mg/kg once/wk i.m) plus endoxifen (0.5 mg-2 mg)/mouse per day, 5 days/week by gavage; (iv) withdrawal of E2D support.

Suppression of tumor growth in this breast cancer tumor model is indicative of therapeutic effect in the treatment of breast cancer in humans (15).

Example 12

Endoxifen Minimizes Uterotrophic Effect of Estrogen

It is known that Tamoxifen is a non-steroidal agent with potent anti-estrogenic effect in animal and in vitro models. This pharmacologic property is related to the drug's ability to compete with estrogen for estrogen receptors in breast tissues, and to inhibit the stimulatory effect of estrogen on the uterus, vagina and ovaries (18).

Endoxifen (0.1 mg-2 mg) is administered orally once daily for 28 days to determine the reduction in utertrophic effect of estradiol; Female BALB/c mice approximately 50 days old and weighing 19-20 g are obtained (e.g., from Charles-River, Inc.) and housed four to five per cage at a temperature (23+_1 C) and light (12 h light/day). The atrophic changes are observed in the mice. There will be three groups such as vehicle control, Tamoxifen and endoxifen. The animals (5-10 mice) are randomly assigned to each group. Daily treatments of intact mice with a dose (e.g., 0.1 mg-2 mg) by gavage of Tamoxifen or endoxifen are expected to lead to progressive inhibition of uterine and vaginal weight.

Such results will show that endoxifen has better minimizing uterotrophic effect of estrogen than Tamoxifen, and that endoxifen finds use as an effective anti-estrogen. Endoxifen blocking of uterine weight gain stimulated by estrogen can also be demonstrated in immature rats. Endoxifen preparations showing the effects described above find use in the treatment of breast cancer as well as other estrogen-sensitive conditions, such as endometriosis, leiomyomata, and benign breast disease, as well as other estrogen-responsive conditions in men and women.

Example 13

Endoxifen-Caused Decrease of Ki-67 Antigen Expression in Proliferating Breast Cancer Cells Ki-67 is a nuclear non-histone protein. This antigen is absent in quiescent cells and is expressed in proliferating cells and is used as a biomarker (19-20). Endoxifen base or endoxifen-citrate in oral or injectable form are given to xenograft breast cancer tumor models (e.g., as described above), as well as to breast cancer patients. Immunochemical determination of Ki-67 is done in tumor cells from breast cancer tissues from patients, as well as from mice bearing tumors as described in Example 11. The MIB-1 or similar antibody available from commercial sources such as DAKO, Carpenteria, Calif. is used for immunochemical localization of antigen. Decrease in Ki-67 antigen expression in animals and/or breast cancer patients demonstrate the applicability of endoxifen in treating breast cancers.

Example 14

Endoxifen Reduces IGF-1 Levels in Breast Cancer

It is known for humans that Tamoxifen reduces the levels of circulating insulin-like growth factor I (IGF-1). IGF-1 has been used as a surrogate biomarker and predicts the effectiveness of Tamoxifen in treatments of breast cancer patients (21). To test the effects of endoxifen preparations of the present invention, endoxifen base or endoxifen-citrate are given orally or injected to experimental animals bearing breast cancer tumors. The concentration of IGF-1 levels in control and xenografted breast tumor is monitored by established assays (e.g., ELISA Kit from Diagnostics Systems Laboratories, London, UK or DAKO, Carpenteria, Calif.). Endoxifen is administered by gavages at 0.5 mg-2 mg per mouse per day, 5 days/week. Decrease of IGF-1 levels and tumor growth reduction indicates the usefulness of IGF-1 as a surrogate marker for breast cancer.

Example 15

Endoxifen Prevents Development of Bicalutamide-Induced Gynecomastia and Breast Pain Bicalutamide (CasodexR) is used for treating prostate cancer in men. There is growing evidence that IGF-1 may be involved in prostate cancer promotion and progression. It is also known that anti-estrogen agents such as Tamoxifen decrease IGF-1 levels and prevent biculatamide-induced gynecomastia in prostate cancer patients (22). Since, endoxifen is an active metabolite of the Tamoxifen anti-estrogen, the silastic slow-release capsules containing endoxifen for implant or oral doses of endoxifen (1 mg-10 mg/day) with biculatamide are expected to prevent development of biclutamide-induced gynecomastia and breast pain.

REFERENCES

Furr B J, Jordan V C. The pharmacology and clinical uses of Tamoxifen. Pharmacol Ther 1984; 25:127-205.
Osborne. Tamoxifen in the treatment of breast cancer. N Engl J Med 1998; 339:1609-18.
Fisher B, Costantino J P, Wickerham D L, Redmond C K, kavanah M, Cronin W M, et al. Tamoxifen for prevention of breast cancer: Report of the National Surgical Adjuvant and Bowel Project P-1 Study. J. Natl Cancer Insts 1998; 90:1371-88.
Stearns V, Ullmer L, Lopez J F, Smith Y, Issacs C, Hays D. Hot flushes. Lancet 2002; 360:1851-61.
Otton S V, Ball S E, Cheung S W, Inaba T, Rudolph R L, Sellers E M. Venlafaxine oxidation in vitro is catalyzed by CYP2D6. Br J Clin Pharmacol 1996; 41:149-56.
Stearns V, Johnson M D, Rae J M, Morocho A, Novielli A, Bhargava P, Hayes D F, Desta Z, Flockhart D A. Active Tamoxifen metabolite concentrations after co-administration of Tamoxifen and the selective serotonin reuptake inhibitor paroxetine. J Natl Cancer Inst 2003; 95:1758-1764.
Y C, Desta Z, Flockhart D A and Skaar T C. Endoxifen (4-hydroxy-N-desmethyl-Tamoxifen) has anti-estrogenic effects in breast cancer cells with potency similar to 4-hydroxy-Tamoxifen. Journal of Cancer Chemotherapy and Pharmacology 2005: 55: 471-478.
Young Chai Lim, Lang Li, Zeruesenay Desta, Qianqian Zhao, James M. Rae, David A. Flockhart, and Todd C. Skaar. Endoxifen, a Secondary Metabolite of Tamoxifen, and 4-OH-Tamoxifen Induce Similar Changes in Global Gene Expression Patterns in MCF-7 Breast Cancer Cells; JPET, 2006, 318:503-512.
Matthew P. Goetz, James M. Rae, Vera J. et al. Pharmacogenetics of Tamoxifen Biotransformation Is Associated With Clinical Outcomes of Efficacy and Hot Flashes. JCO Dec. 20 2005: 9312-9318.
Satyavati G V, Economic and Medical Plant Research, 5, 47(1991).
Indian Pharmacopea, 1988.
Remington: The Science and Practice of Pharmacy (Lippincott Williams & Wilkins (2000), pages 836-58.
Percutaneous Absorption: Drugs Cosmetics Mechanisms Methodology edited by Bronaugh and Maibach, Marcel Becker Publisher (1999).
Stephen R. D. Johnston, Irene M. Boeddinghaus, Sharon Riddler, Ben P. Haynes, Ian R. Hardcastle, Martin Rowlands, Rachel Grimshaw, Michael Jarman, and Mitch Dowsett. Iodoxifen Antagonizes Estradiol-dependent MCF-7 Breast Cancer Xenograft Growth through Sustained Induction of Apoptosis, Cancer Research, 59, 3646-3651 (1999).
Iino, Y, Wolf, D M, Langan-Fahey S M, Johnson, D A, Ricchio, M, Thompson, M E, and Jordan V C. Reversible Control of Oestradiol-stimulated Growth of MCF-7 Tumours in the Athymic Mouse. Br. J. cancer, 64: 1019-1024 (1991)
Jann N Sarkaria, David F C Gibson, V C Jordan, John F Fowler, Mary J. Lindstrom, and R. Timothy Mulacahy. Tamoxifen-induced increase in the Doubling time of MCF-7 Xenografts as Determined by Bromodeoxyuridine Labeling and Flow Cytometry. Cancer Research 53, 4413-4417 (1993).
Nanjoo Suh, Andrew L. Glasebrook, Alan D. palkowitz, Henry U. Bryant, Lorris L. Burris, james J. Starling, Homer L. Pearce, Charlotte Williams, Christopher Peer, Yongping Wang and Michael B. Sporn. Arzoxifene, a New Selective Estrogen receptor Modulator For Chemo prevention of Experimental Breast Cancer. Cancer Research 61, 8412-8415 (2001).
Assersohn L, Salter J, Powles T J, et al: Studies of the potential utility of Ki-67 as a predictive molecular marker of clinical response in primary breast cancer. Breast Cancer Res Treat 82:113-123, (2003).
Kenny F S, Willsher P C, Gee J M, et al: Change in expression of ER, bcl-2 and MIB-1 on primary Tamoxifen and relation to response in ER positive breast cancer. Breast Cancer Res Treat 65: 135-144, (2001).
Nahta R, Hartobagyi G N and Esteva F J. Growth factor Receptors in Breast Cancer: Potential for Therapeutic Intervention, Oncologist 8: 5-17, (2003).
Saltstein D, Sieber P, Morris T, Gallo J. Prevention and Management of Biclutamide-induced gynecomastia and Breast Pain: Randomized Endocrinologic and Clinical Studies with Tamoxifen and Anastrozole. Prostate cancer and Prostatic Diseases 8, 75-83 (2005).

The invention claimed is:
1. A method of delivering endoxifen to the plasma of a subject, comprising orally administering to the subject an enteric-coated tablet or enteric-coated capsule containing a pharmaceutical composition comprising an amount of a synthetic preparation of endoxifen effective to deliver endoxifen to the plasma of the subject, wherein:
   i) said synthetic preparation of endoxifen is at least 80% Z-endoxifen; and
   ii) said synthetic preparation of endoxifen is in the form of a citrate salt.

* * * * *